(12) United States Patent
Bienhaus et al.

(10) Patent No.: US 7,537,935 B2
(45) Date of Patent: May 26, 2009

(54) SYSTEM FOR PROVIDING BIOLOGICAL MATERIALS

(75) Inventors: Gerhard Bienhaus, Wielenbach (DE); Michael Fritz, Biblis (DE); Jurgen Schwab, Ketsch (DE); Thomas Walter, Penzberg (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 984 days.

(21) Appl. No.: 10/694,136

(22) Filed: Oct. 27, 2003

(65) Prior Publication Data

US 2004/0092030 A1 May 13, 2004

Related U.S. Application Data

(63) Continuation of application No. 09/485,144, filed on Oct. 2, 2000, now Pat. No. 6,669,910.

(51) Int. Cl.
  *B01D 15/08* (2006.01)
  *G01N 33/53* (2006.01)
  *G01N 1/18* (2006.01)
(52) U.S. Cl. .............. 436/177; 210/198.2; 210/232
(58) Field of Classification Search ............ 210/321.75, 210/198.2, 232; 436/177; 536/25.41
See application file for complete search history.

(56) References Cited

U.S. PATENT DOCUMENTS

| | | | | |
|---|---|---|---|---|
| 3,713,771 A | | 1/1973 | Taylor et al. ............ | 141/378 |
| 4,142,858 A | * | 3/1979 | Acuff ..................... | 436/67 |
| 4,479,720 A | * | 10/1984 | Mochida et al. .......... | 366/214 |
| 4,683,058 A | | 7/1987 | Lyman et al. ........... | 210/359 |
| 4,735,318 A | | 4/1988 | Keffeler et al. .......... | 206/532 |
| 4,741,441 A | | 5/1988 | Keffeler ................. | 206/532 |

(Continued)

FOREIGN PATENT DOCUMENTS

DE  41 24 778 A1  1/1993

(Continued)

OTHER PUBLICATIONS

"Rapid Nucleic Acid Purification for Reliable PCR", News Qiagen, Issue No. 1/94, pp. 9-10.

(Continued)

*Primary Examiner*—Jill Warden
*Assistant Examiner*—Lore Ramillano
(74) *Attorney, Agent, or Firm*—Olga Kay; Charles M. Doyle (57) ABSTRACT

A process and closure arrangement is provided for isolating purified biological material. The process includes placing biological materials in separate lysis vessels, adding lysis liquids to the biological materials in the lysis vessels, and transferring the liquids in the lysis vessels into a matrix unit. The liquids in the matrix vessels of the matrix unit are extracted through outlet openings during which the liquids flow through matrices and the matrix unit is placed on a collecting unit with collecting vessels which are arranged such that at least the outlet openings of the matrix vessels extend into the collecting vessels. The matrix vessels are with elution fluid and elution fluids from the matrix vessels are extracted through their outlet openings during which the elution fluids flow through the matrices and the elution fluids which are enriched with biological material are collected in the collecting vessels.

5 Claims, 12 Drawing Sheets

U.S. PATENT DOCUMENTS

| | | | |
|---|---|---|---|
| 4,793,492 A | 12/1988 | Halbich | 206/538 |
| 4,810,471 A | 3/1989 | Wachob et al. | 422/103 |
| 4,895,706 A | 1/1990 | Root et al. | 422/102 |
| 4,948,564 A | 8/1990 | Root et al. | 422/101 |
| 4,956,298 A | 9/1990 | Diekmann | 430/311 |
| 5,037,544 A | 8/1991 | Snyder | 210/198.2 |
| 5,141,719 A | 8/1992 | Fernwood et al. | 210/323.1 |
| 5,219,528 A | 6/1993 | Clark | 422/101 |
| 5,264,184 A | 11/1993 | Aysta et al. | 422/101 |
| 5,398,837 A | 3/1995 | Degrassi | 220/337 |
| 5,417,923 A | 5/1995 | Bojanic et al. | 422/101 |
| 5,538,849 A * | 7/1996 | Uematsu et al. | 435/6 |
| 5,603,899 A | 2/1997 | Franciskovich et al. | 422/100 |
| 5,645,723 A * | 7/1997 | Fujishiro et al. | 210/321.75 |
| 5,683,659 A | 11/1997 | Hovatter | 422/102 |
| 5,785,925 A | 7/1998 | U'Ren | 422/72 |
| 5,806,670 A | 9/1998 | Harlan et al. | 116/67 R |
| 5,888,831 A | 3/1999 | Gautsch | 436/177 |
| 5,910,246 A | 6/1999 | Walter et al. | 210/232 |
| 5,948,363 A | 9/1999 | Gaillard | 422/102 |
| 6,017,698 A | 1/2000 | Bienhaus et al. | 435/6 |

FOREIGN PATENT DOCUMENTS

| | | |
|---|---|---|
| DE | 41 27 276 C2 | 10/1993 |
| DE | 41 43 394 C2 | 5/1994 |
| DE | 196 05 814 A1 | 8/1997 |
| EP | 0 734 768 A1 | 2/1996 |
| EP | 0 738 733 A2 | 10/1996 |
| WO | WO 91/07648 | 5/1991 |
| WO | WO 93/01739 | 2/1993 |
| WO | WO 96/31781 * | 10/1996 |
| WO | WO 97/11155 | 3/1997 |

OTHER PUBLICATIONS

"New: QIAamp for Tissue and Mouse Tails", News Qiagen, Issue No. 2/94, pp. 9-11.

* cited by examiner

SYSTEM FOR PROVIDING BIOLOGICAL MATERIALS

CROSS-REFERENCE TO RELATED APPLICATIONS

This application is a continuation of U.S. patent application Ser. No. 09/485,144, having a filing date of Oct. 2, 2000 now U.S. Pat. No. 6,669,910 and claims priority under 35 U.S.C. 119 of German Application Serial No. 197 34 135.7 filed Aug. 7, 1997.

FIELD OF THE INVENTION

The present invention concerns a system which enables the user to process biological samples by contacting the sample with a matrix which binds the desired biological materials and subsequently eluting the biological materials from the matrix. This method of isolating biological materials is used especially in the field of cell analysis or nucleic acid analyses where relatively small amounts of biological materials are required.

BACKGROUND AND SUMMARY OF THE INVENTION

Figure 1:
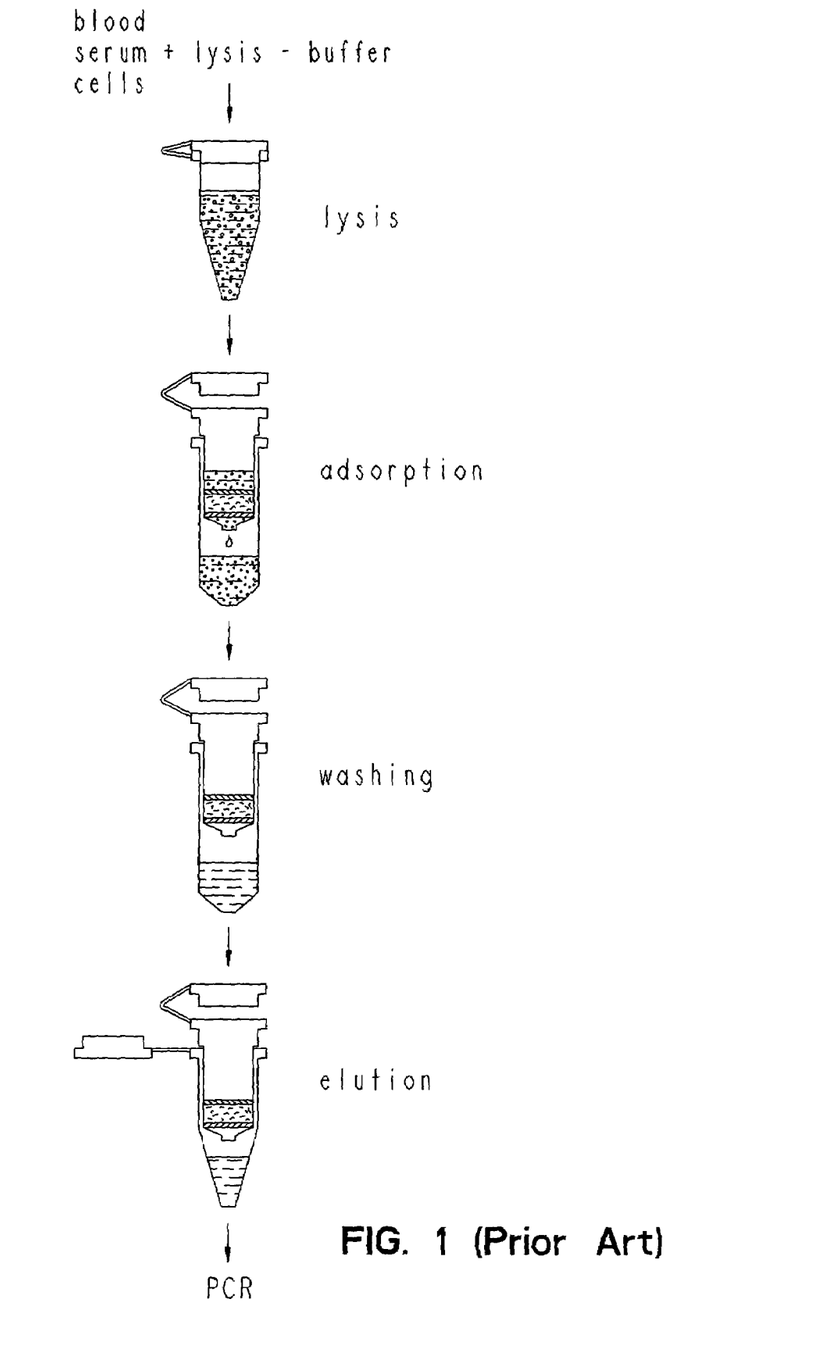
FIG. 1 is a diagrammatic view of a so-called QUIamp kit.

Devices are already known in the prior art, which use matrices to bind and purify nucleic acids. For example a vessel is described in EP-A-0 738 733 into which a liquid sample can be added which has a porous matrix on its underside to which nucleic acids can be bound by drawing the sample through the matrix. In addition a device is described in DE-4143394 which has a plurality of vessels arranged next to one another which have a layer of selectively adsorbing material at the bottom and an outlet opening on the underside of the vessels. The described arrangement of vessels is placed on a unit of sample holding vessels such that liquid from the former vessels pass into the collecting vessels after passage through the layer of adsorbing material. Furthermore the so-called QUIamp kit is known from the Quiagen Company whose function is shown in FIG. 1. Firstly a sample liquid together with a lysis buffer is added to a sealable vessel and a lysis of the mixture is carried out. In the subsequent step the lysis mixture is added to a vessel containing a matrix capable of specific binding and is drawn through the matrix by centrifugation and the emerging liquid is collected in a vessel. The matrix is subsequently washed and finally the adsorbed biological material is eluted.

A disadvantage of the prior art is that the user who is usually confronted with a large number of different samples has little support in automating his processes. In the system of the prior art shown in FIG. 1 individual vessels are used to process the sample so that when several samples are processed in parallel individual vessels are always present which can easily be mixed up. In contrast labelling each vessel means some work for the operator so that it is often not done. Mixing up samples can have disastrous consequences especially when processing nucleic acids which is frequently used to detect diseases or for criminal investigations.

There is still no known concept in the prior art, which would suitably assist a user with a large number of samples either by accelerating the manual processing or automating the processing.

Hence an object of the present invention was to propose a system for providing biological materials, which enables a coordinated, simple processing of a plurality of sample materials which prevents mistakes and contamination. A further object of the present invention was to provide a system and process, which can adequately exclude the possibility of mistaking samples. A further aspect of the present invention relates to the problem of providing a closure design, which takes into account the specific requirements needed to provide biological materials.

The above objects are achieved by a process for isolating a purified biological material comprising the following steps:
 a) Placing biological materials in separate lysis vessels of a lysis unit comprising two or several lysis vessels in a predetermined geometric arrangement,
 b) adding lysis liquids to the biological materials in the lysis vessels,
 c) transferring the liquids in the lysis vessels into a matrix unit containing matrix vessels with outlet openings whose number corresponds to the number of lysis vessels which are arranged in a predetermined geometric arrangement and a matrix is located in each of the matrix vessels to which the biological material to be purified binds,
 d) extracting the liquids in the matrix vessels through the outlet openings during which the liquids flow through the matrices,
 e) placing the matrix unit on a collecting unit with collecting vessels which are arranged such that at least the outlet openings of the matrix vessels extend into the collecting vessels,
 f) filling the matrix vessels with elution fluid,
 g) extracting the elution fluids from the matrix vessels through their outlet openings during which the elution fluids flow through the matrices and the elution fluids which are enriched with biological material are collected in the collecting vessels.

The process mentioned above for obtaining purified biological materials has the advantage over the prior art that it enables the processing steps to be systematized due to the predetermined geometric arrangements of the lysis unit, matrix unit and collecting unit. The predetermined geometric arrangement of the lysis vessels, which preferably corresponds to the geometric arrangement of the matrix vessels in the matrix unit makes it easier for the user to transfer a lysed biological material from a collecting vessel into the corresponding matrix vessel. Furthermore the arrangement of matrix vessels corresponds to that of the collecting vessels in such a manner that at least the outlet openings of the matrix vessels extend into the collecting vessels when the matrix unit is placed on the collecting unit.

The assembly of lysis vessels, matrix vessels and collecting vessels which forms the corresponding units has the additional advantage that it is not necessary to handle individual vessels but rather whole units can be moved whose size and shape are much easier to handle.

In the said process it is additionally possible to use codes on the individual units, which enable a sample placed in a lysis vessel to be unambiguously assigned to the eluate that is finally collected.

Figure 2:
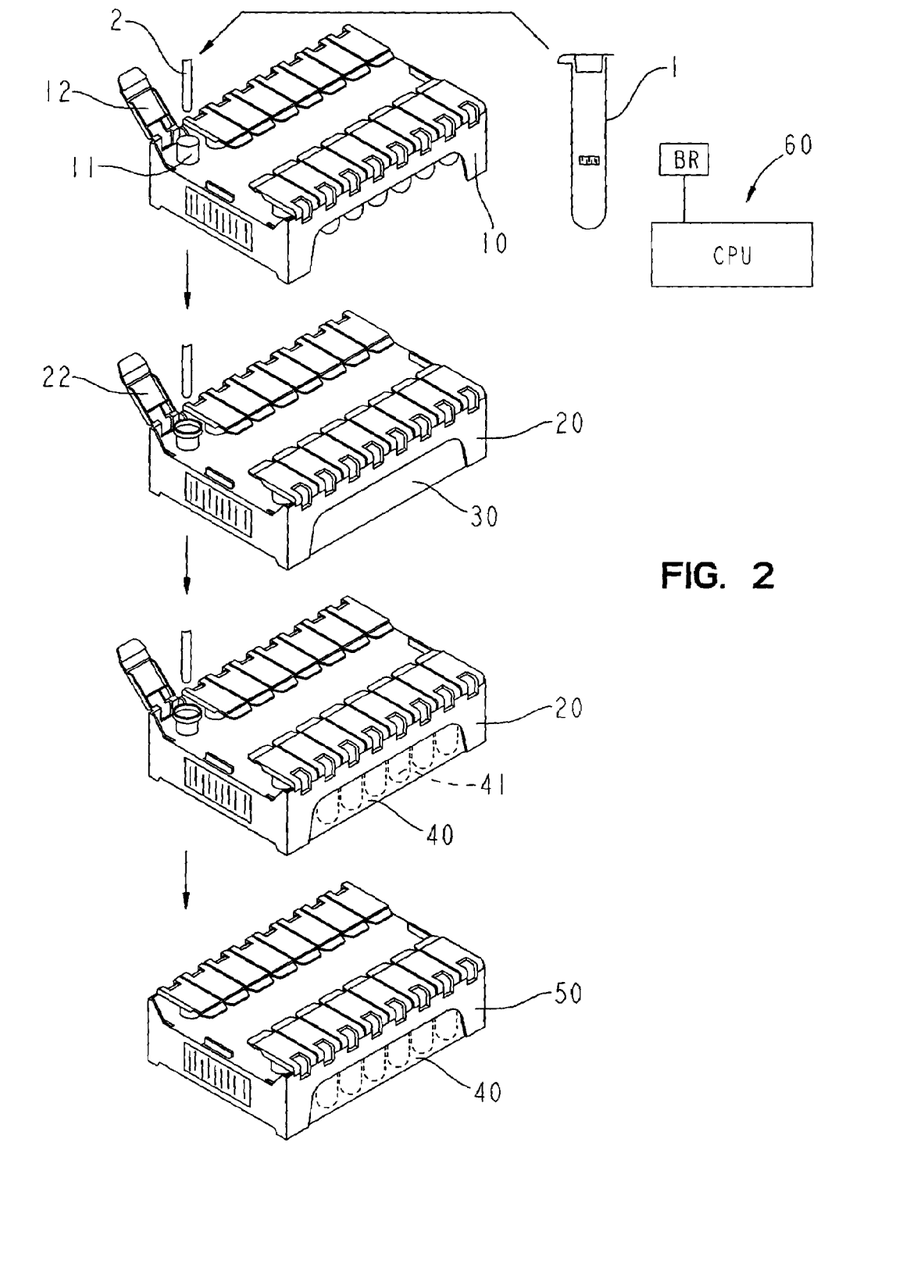
FIG. 2 is a diagrammatic view of the process of the present invention.

The above-mentioned process is further elucidated by FIG. 2.

FIG. 2 shows a sample (1), which is placed in a lysis vessel (11) of the lysis unit (10) using a pipette (2). A lysis liquid is also added to the same lysis vessel (11). The other lysis vessels of the lysis unit (10) can be filled with other sample liquids and with the same or other lysis liquids. The lysis unit (10) has closures (12) that are used to close the lysis vessels and whose number corresponds to the number of lysis vessels. Preferably only the respective lysis vessel to which the liquid is added is opened during the pipetting steps to exclude contamination of the other lysis vessels for example by falling drops. The construction of the lysis unit is elucidated later in more detail by FIGS. 3A and 3B. At this point only the sample and reagents as well as the process steps are described in detail.

Sample materials which can be processed with the present invention are for example liquids such as blood, saliva etc.; it is however, also possible to use solid samples such as e.g. pieces of tissue etc.

Lysis liquids are known in the prior art and they are usually alkaline solutions of alkyl sulphates or other compounds that damage the cell walls. Cell walls of cells contained in the sample are destroyed during lysis to release the cell contents and in particular nucleic acids. For this the mixture of sample and lysis liquid is usually incubated for a period of a few minutes at an elevated temperature such as 70° C. The mixture obtained is referred to as the lysis mixture in the following.

DETAILED DESCRIPTION OF THE INVENTION

FIG. 2 also shows a combination of a matrix unit (20) and a waste unit (30). After the sample has been lysed in the lysis unit (10), the lysis mixture is pipetted from a lysis vessel into a matrix vessel (21) of the matrix unit (20). The pipetting from the lysis unit into the matrix unit is preferably carried out such that the pipetting takes place between corresponding vessels i.e. a pipetting is carried out from vessel 1 of the lysis unit into vessel 1 of the matrix unit. For this purpose the lysis and matrix unit are preferably provided with numbers, letters or such like that enable corresponding vessels to be put in order. The aforementioned pipetting step is also preferably carried out such that only the cap (22) of the vessel into which the liquid is to be pipetted is opened. This also avoids a contamination of the other matrix units. The waste unit (30) with cavities into which the liquid emerging from the matrix vessels is collected is located below the matrix unit. The matrix unit (20) is placed on the waste unit (30) in such a manner so that each of the matrix vessels extends into a corresponding cavity of the waste unit. This prevents mixing of liquids emerging from different matrix vessels. This could be tolerated if it could be ensured by an adequate depth of the construction and appropriate procedures that the matrix vessels do not come into contact with the liquid mixture and that the matrix is not contaminated with foreign sample materials. However, in order to maintain a small depth of the construction and to avoid contamination of the matrix vessels, an individual cavity is preferably provided for each of the matrix vessels. In addition it is advantageous to cover the cavities with an absorbent material for example a fleece, which absorbs the waste liquids so that no movement of liquid occurs during transport that could lead to contamination of the matrix.

The added lysis mixture can for example be removed from the matrix vessels (21) by applying negative pressure to the cavities (35) of the waste unit (30) or by applying positive pressure to the inlet openings (27) of the matrix vessels (21). However, the system shown in FIG. 2 is designed such that the lysis mixture can be removed in a simple manner from the outlet openings (28) of matrix vessels (21) by centrifugation. For this the arrangement of matrix unit (20) and waste unit (30) filled with lysis liquids is placed in a centrifuge and the fluids are moved through the matrices (29) by centrifugal force. The size of the arrangement is preferably such that it can be used in centrifuges suitable for microtitre plates. As the liquids pass through the matrices (29) of the matrix vessels (21) the biological materials to be purified are adsorbed to the matrices. It is well known in the prior art which types of matrices can be used for various materials to be adsorbed. Glass fibre fleeces can for example be used for nucleic acids. Reference is made to EP-A-0 738 733 for further details concerning matrix vessels and the matrices used therein. The binding of the biological materials to be isolated to the matrix is primarily adsorptive i.e. it is based on a physical binding. However, the invention also encompasses those binding processes in which an ionic or covalent bond is formed between the biological materials to be isolated and the matrix material.

After the lysis liquid has been centrifuged through the matrices, the matrices can be washed by adding washing liquid (for example distilled water) and centrifuging again. Such washing processes can be repeated several times as required. The system composed of matrix unit and waste unit does not have to be removed from the centrifuge for this; on the contrary washing liquid can be added directly to the matrix vessels while the centrifuge is at standstill.

After the lysis liquids and optionally subsequent washing liquids have been removed from the matrix vessels, the matrix unit (20) is removed from the waste unit (30) and placed on a collecting unit (40). The collecting unit (40) has a number of collecting vessels (41) which corresponds to the number of matrix vessels. The matrix unit and collecting unit are designed such that at least the outlet openings of the matrix vessels extend into the collecting vessels when the matrix unit is placed on the collecting unit. Elution fluids are added to the matrix vessels in order to detach the biological substances to be isolated and are pressed through the matrices into the collecting vessels, which is preferably carried out by centrifuging the arrangement of matrix unit and collecting unit. Suitable elution fluids for the elution are matched to the materials to be eluted and the matrix material. Elution fluids are well known in the prior art and reference is made for example to EP-A-738 733.

After the elution purified biological materials are present in the collecting vessels of the collecting unit (40), which can be used for further steps such as the polymerase chain reaction. In a particularly advantageous embodiment of the process according to the invention the matrix unit (20) is removed after the elution from the collecting unit (40) and the closure unit (50) is placed on the collecting unit (40). The closure unit (50) has a number of connecting tubes which corresponds to the number of collecting vessels and which make a liquid-tight joint with the collecting vessel when the closure unit is put on. The top of the connecting tubes is closed by caps. In this manner the collecting unit with open vessels can be completely closed in one handling step. A particular advantage of this type of closure is that the individual collecting vessels can be opened individually and thus contaminations can be completely avoided if the work is carried out carefully.

FIG. 2 additionally shows a coordination unit (60) with a bar code reader (BR) and a comput0ng and storage unit (CPU). According to the present invention a process for isolating purified biological materials can be advantageously carried out by firstly storing the data for a sample. This can for example be achieved by reading a bar code on the sample or also by manually entering the data into the storage and computing unit. In such a process a code is attached to the lysis unit which identifies the entire unit. When a sample is added to a lysis vessel of the lysis unit, the position of the sample within the lysis unit and the code of the lysis unit is entered into the computing and storage unit. The latter can for example be achieved by reading the code with a bar code reader (BR). When the lysis liquid from the lysis unit (10) is transferred into the matrix unit (20) the coordination unit registers from which lysis unit and into which matrix unit the transfer takes place. For this purpose the coding of the matrix unit is assigned to the code for the lysis unit within the coding unit. Furthermore the liquid transfer takes place in a coordinated manner i.e. liquid is transferred from one vessel of the lysis unit (10) into the corresponding vessel of the matrix unit. The corresponding vessels in the lysis and matrix unit can be recognized by the user on the basis of the position of the vessel within the unit. The units are preferably additionally provided with numbers, letters, colours or the like which allow the user to identify corresponding vessels.

There may also be a code on the collecting unit (40), which is allocated to the code of the matrix unit. However, a code on the closure unit is preferably used in order to monitor the position of the samples. The individual allocation steps enable an unequivocal allocation of an elution fluid to the sample from which it has been eluted by means of the code on the collecting unit or the code on the closure unit (50) and the position within the collecting unit. The described coding concept which is based on a constant geometric arrangement of the vessels in the individual units, the codes on the individual units and a coordinated transfer of the liquids thus enables a simple and reliable allocation of the elution fluids to the original samples. The described concept achieves a high degree of security against mistakes with little work for the user. Within the scope of the present invention a geometric arrangement is understood as an arrangement in which several vessels of a unit are arranged at a regular distance to one another. This is in particular understood as linear arrangements or arrangements of the vessels in a rectangular shape. Such arrangements enable a systematic processing by the user and thus ensure a rapid and reliable operation.

The process of the present invention can additionally be advantageously carried out with hinged caps on the lysis unit, matrix unit and/or closure unit, which can take up the following three positions:

An opened position in which liquid is added and removed,
a position in which the cap is lowered and rests on the opening of the vessel below,
a closed position in which the cap's vessel is closed and from which the cap can only be moved into the open position by force or after releasing a fastener.

A process according to the invention can be carried out with such caps in which the caps are in the lowered position before adding liquid, then the respective cap of the vessel where an addition is to be made is opened and the cap is completely closed after the addition. In this procedure the difference between lowered and completely closed caps enables the user to identify in which vessels an addition has already taken place and which still have to be processed.

The present invention additionally concerns a system for providing biological materials comprising
a) a collecting unit for collecting the biological material which has two or several collecting vessels each of which has an opening which is accessible from above,
b) a matrix unit with a holder in which the matrix vessels are located which have an inlet opening for adding a fluid as well as an outlet opening for discharging fluid and the matrix vessels are arranged such that at least their outlet openings extend into the collecting vessels when the matrix unit is placed on the collecting unit,
c) a closure unit which is placed on the collecting unit and which has a number of connecting tubes, which corresponds to the number of collecting vessels and these tubes have a connecting opening and a discharge opening closed with a cap and connecting tubes with their connecting openings are attached to the collecting vessels in a water-tight manner when the closure unit is placed on the collecting unit.

Figure 6:
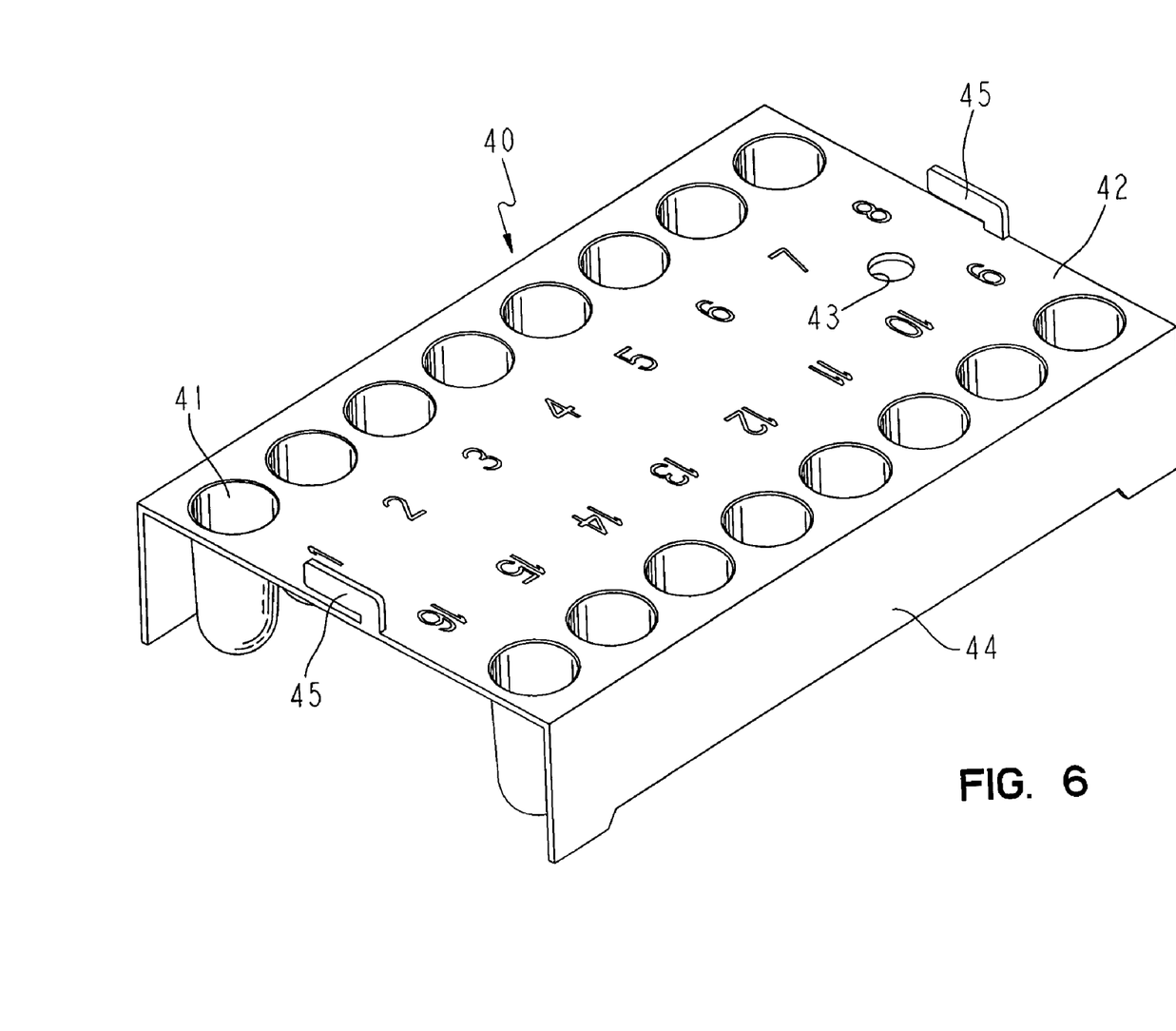
FIG. 6 shows a perspective view of a collecting unit.

The said system facilitates the operations that have to be carried out by the user when providing biological materials by the use of the collecting unit, matrix unit and closure unit. In particular the system differs from the prior art in that a separate closure unit is used, which is placed on the collecting unit to seal the collecting vessels. Whereas individual vessels are used in the prior art (see e.g. FIG. 1), which have to be individually manipulated by the user, the present system facilitates the operating steps of the user by arrangements, which have several processing vessels of the same type in a predetermined geometric arrangement. A particular advantage of the system according to the invention is that the collecting unit with its opened collecting vessels can be closed in one handling step. FIG. 6 clearly shows that the collecting unit according to the invention has no cover and thus can be easily placed under the matrix unit (20). However, assembly of the collecting vessels shown in FIG. 1 to form a unit of several collecting vessels does not lead to the collecting unit of the present invention. The use of a separate closure unit with connecting tubes, which are connected to collecting vessels is not described in the prior art.

The system according to the invention can additionally include a lysis unit, a waste unit and/or a coordination unit.

The aforementioned units of the system according to the invention are described in more detail with reference to FIGS. 3 to 9.

Figure 3A:
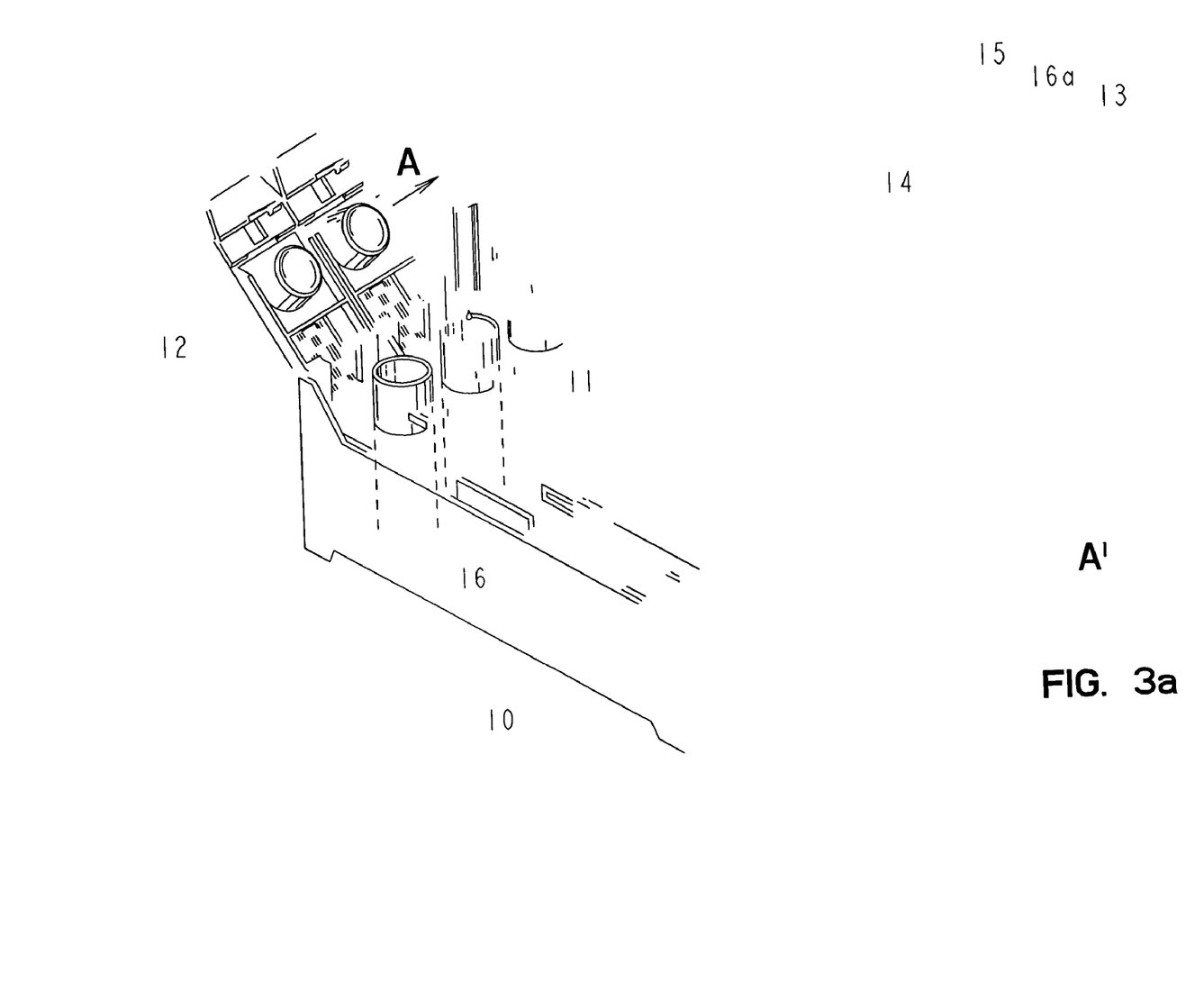
FIG. 3a shows a lysis unit in a perspective view.

FIG. 3a shows a lysis unit in a perspective view. The lysis unit (10) shown has two rows of eight lysis vessels (11) each of which are closed by caps (12). The whole lysis unit can be manufactured as a connected moulded article in an injection moulding process. Hence suitable materials for the lysis unit are for example plastics which can be processed in an injection moulding process such as polyethylene and polypropylene. The wall thickness of the lysis unit can be adapted to the required boundary conditions such as adequate rigidity and heat conduction. Wall thicknesses between 0.5 and 1.5 mm have given satisfactory results in practice.

FIG. 3a also shows a removable rail (13) which is pushed over the ends of the caps and joins one row of caps together. This rail enables the connected caps to be simultaneously opened and closed. However, without the rail (13) the caps (12) can be operated completely independently of one another to enable an independent processing of the lysis vessels. It is of particular advantage when the other lysis vessels are closed by the caps when liquids are added or removed. It is advantageous to use caps (12), which have three positions. In the first position the cap is open to allow addition and removal of liquids from the lysis vessel. The cap is lowered onto the lysis vessel in a second position so that the vessel contents cannot be contaminated by dripping liquid or such. The cap is completely closed in a third position for which the cap is either moved over a barrier or closed by a catch.

FIG. 3a additionally shows a tapered pin (14) which extends downwards from the plate (15). The tapered pin is located on one side of the lysis unit which makes it asymmetric. Interaction of the tapered pin (14) with a corresponding recess in a holder unit or such enables a well-defined positioning of the lysis unit relative to a holder unit or such.

Recesses (16, 16A) are located on the sides of the plate (15), which can also be used to position the lysis unit.

Figure 3B:
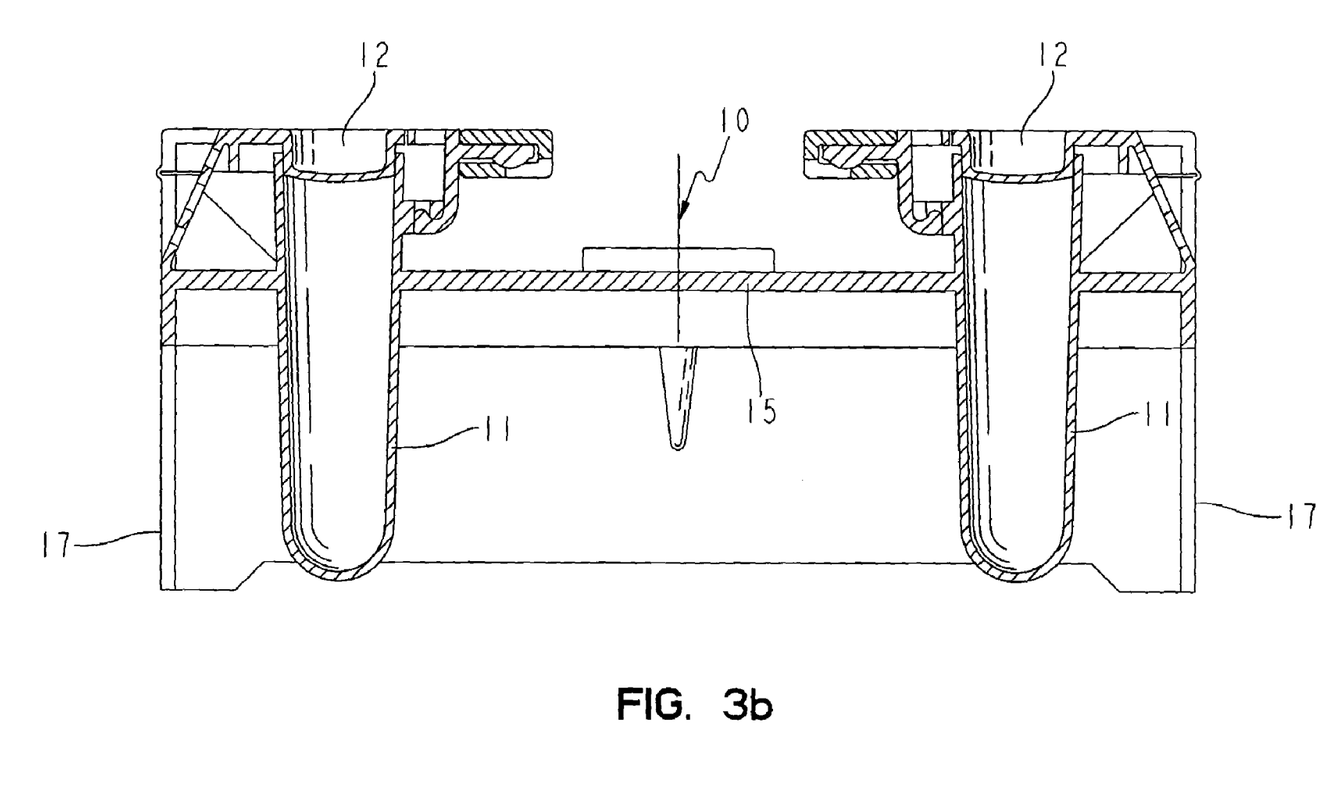
FIG. 3b shows a cross-section through FIG. 3a along the line A-A'.

FIG. 3b shows a cross-section through FIG. 3a along the line A-A'. In this figure it can be seen that the lysis vessels (11) are recessed into the plate (15) such that a part of the vessel is below and another part is above the plate. The lysis vessels typically have a volume of several milliliters. However, the volume can be adapted according to needs. As shown in FIG. 3b the vessels are closed by caps (12). A more accurate description of a particularly suitable cap design for providing biological materials is given in connection with FIG. 9.

FIG. 3b also shows that standing elements (17) are connected to the plate (15) which are preferably long enough to extend below the bottoms of the vessels. The standing elements enable the lysis unit to be placed on a flat surface.

Figure 4A:
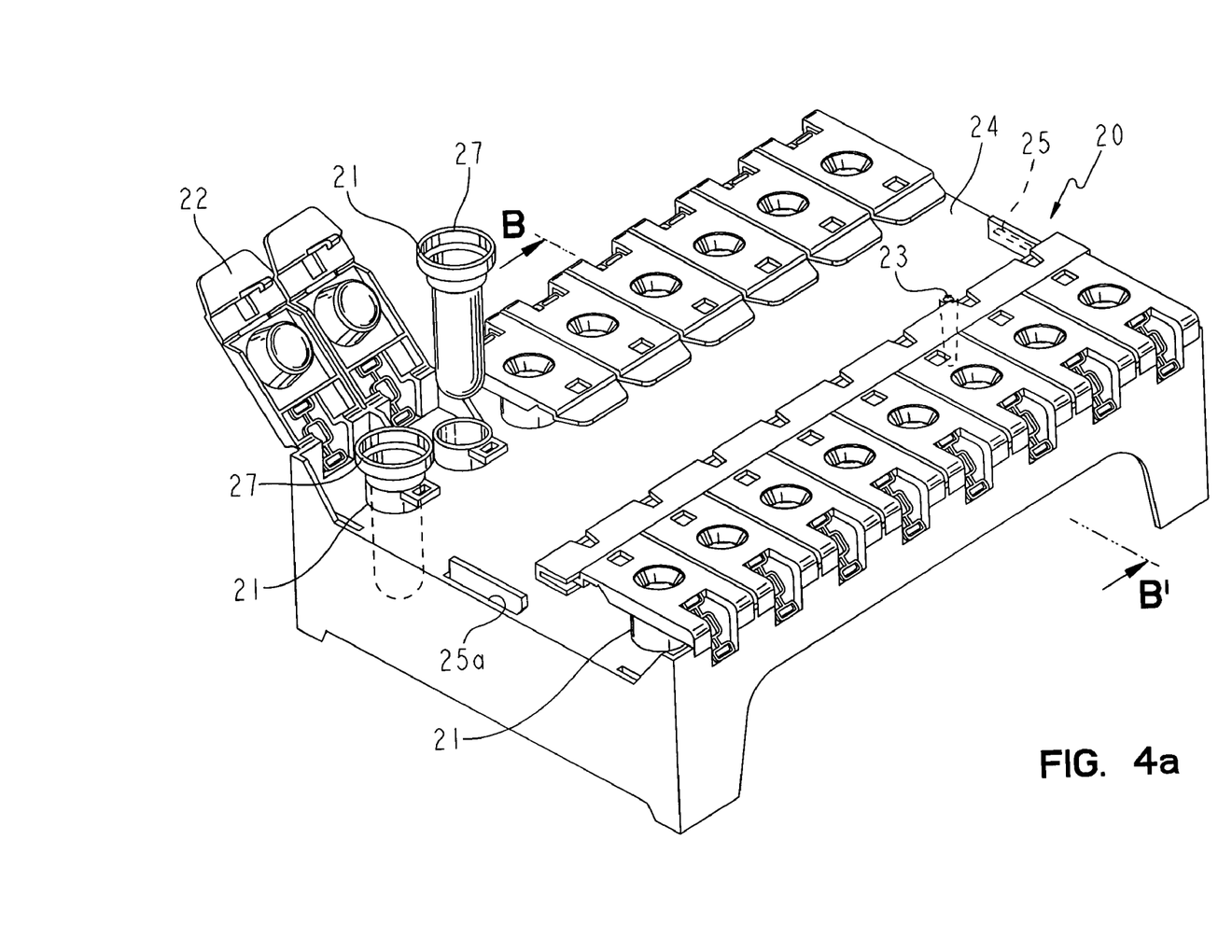
FIG. 4a shows a matrix unit, which has two rows of eight matrix vessels.

A matrix unit is shown in FIG. 4a, which has two rows of eight matrix vessels (21). The matrix vessels (21) can preferably be removed from the matrix unit (20) so that they can be manufactured separately. Each of the matrix vessels is allocated a cap (22), which can be used to close the upper opening of the matrix vessel (application opening). The matrix unit preferably additional has a tapered pin (23), which extends downwards from the plate (24). In addition there are recesses (25, 25a) in the plate (24). The tapered pin and recesses are used to position the matrix unit relative to the collecting unit when the matrix unit is placed on this unit.

Figure 4B:
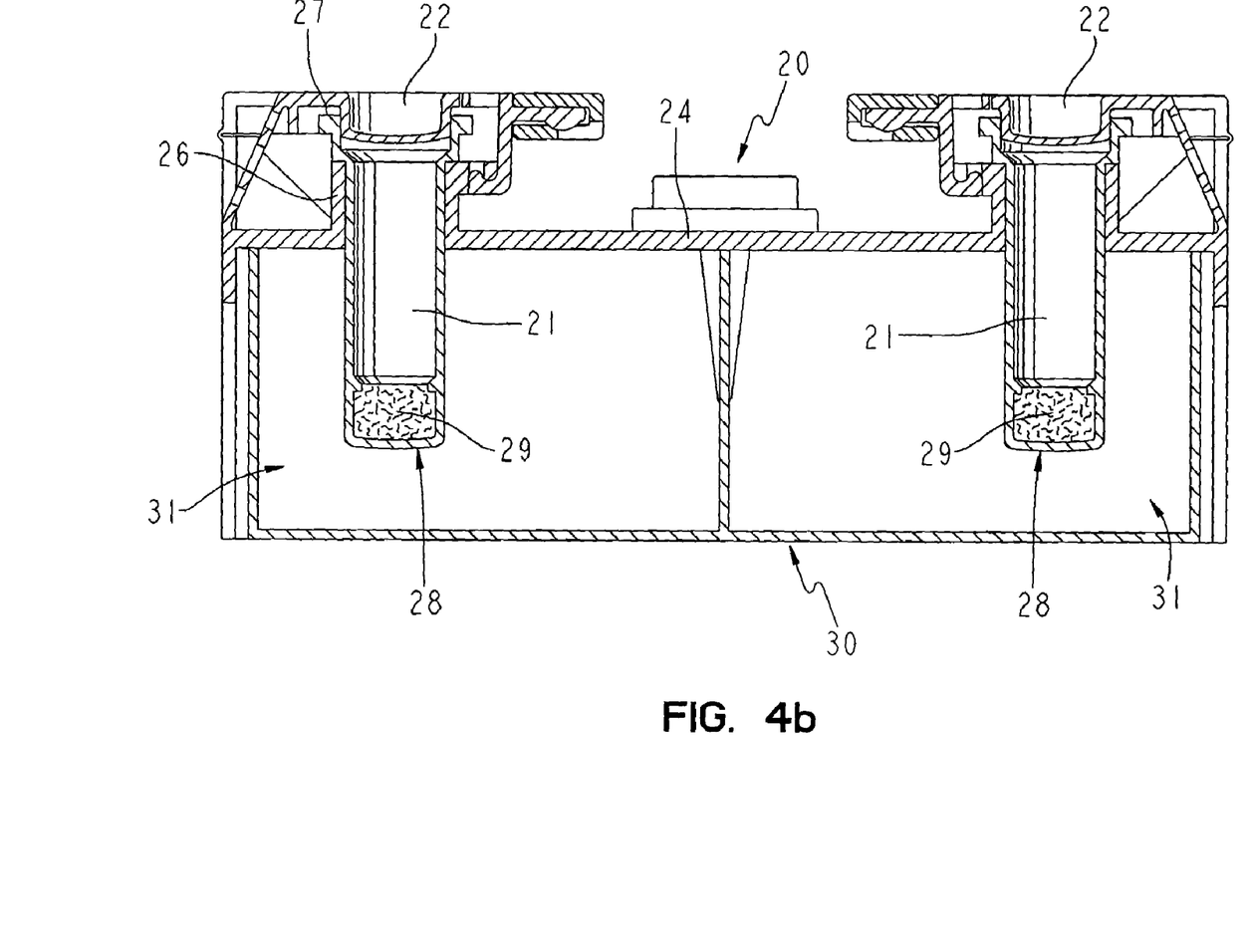
FIG. 4b is a cross-section through FIG. 4a along the line B-B'.

FIG. 4b is a cross-section through FIG. 4a along the line B-B'. Furthermore FIG. 4b shows an arrangement in which the matrix unit is arranged above the waste unit (30). The waste unit (30), which is shown in more detail in FIG. 5, has an individual chamber for each matrix vessel into which the matrix vessel extends. Liquid, which emerges from the matrix vessel through the lower opening (outlet opening) thus passes directly into the corresponding chamber of the waste unit. The relative positioning of matrix unit and waste unit is achieved by positioning elements. This positioning can be advantageously achieved by the matrix unit enclosing the waste unit with its standing elements as is for example the case with the lid of a box.

The matrix vessels in the embodiment shown in FIG. 4 are hung in holes. These holes are located in holders (26) that rise up from the plate (24). There is an expansion of the matrix vessels (21) in the region of the application opening, which rests on the rim of the holder (26).

Matrix vessels, which are suitable for use in the present invention have a material in the region of their outlet openings which can specifically bind the biological materials to be isolated. The materials are preferably porous so that liquid, which emerges from the matrix vessel (21) can flow through them. Suitable materials are described in EP-A-0 738 733. In addition suitable constructions of matrix vessels are mentioned in the said European Patent Application.

Figure 5:
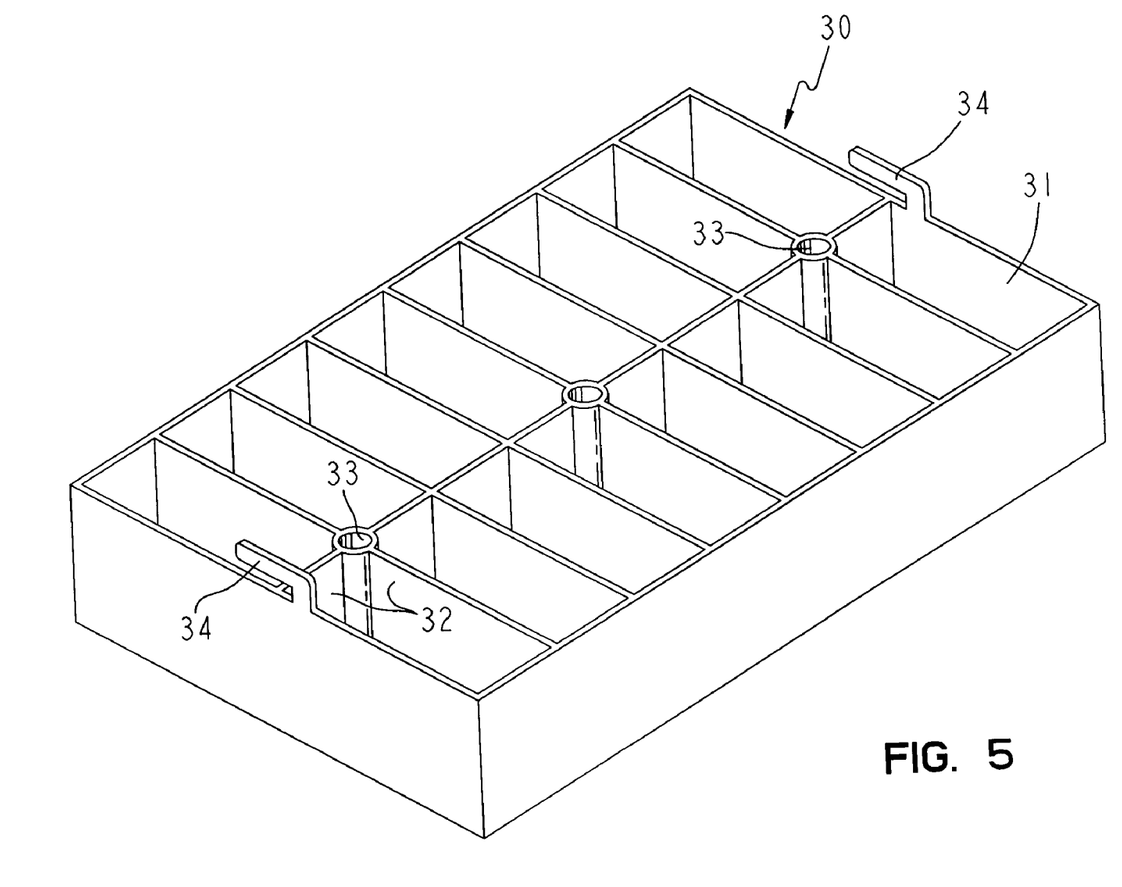
FIG. 5 shows a perspective view of a waste unit.

FIG. 5 shows a perspective view of a waste unit. The waste unit (30) has two rows of eight cavities (31) to receive waste liquids. The cavities (31) are separated from one another by partitions (32) so that the waste liquids cannot mix. The waste unit additionally has the tubes (33) into which the tapered pin (23) of the matrix unit (20) is inserted. Since the waste liquids are discarded, the relative orientation of the matrix unit and waste unit is unimportant so that two tubes (33) are provided to simplify the handling for the user. The waste unit can additionally have tongues (34), which engage in the slots (25, 25a) of the matrix unit when it is mounted on the waste unit.

FIG. 6 shows a perspective view of a collecting unit. The collecting unit (40) has two rows of eight collecting vessels (41). The collecting unit is preferably designed as one piece i.e. the collecting vessels (41) and the holder (42) form an integral unit. In order to unequivocally position the matrix unit on the collecting unit, the collecting unit has a hole (43) into which the tapered pin (23) of the matrix unit engages when the matrix unit is placed on the collecting unit. The interaction between the tapered pin (23) and hole (43) achieves an unequivocal allocation of the matrix vessels to the collecting vessels. The collecting unit additionally has standing elements (44) to place it on a surface and tongues (45) which engage in the slots (25, 25a) of the matrix unit.

Figure 7:
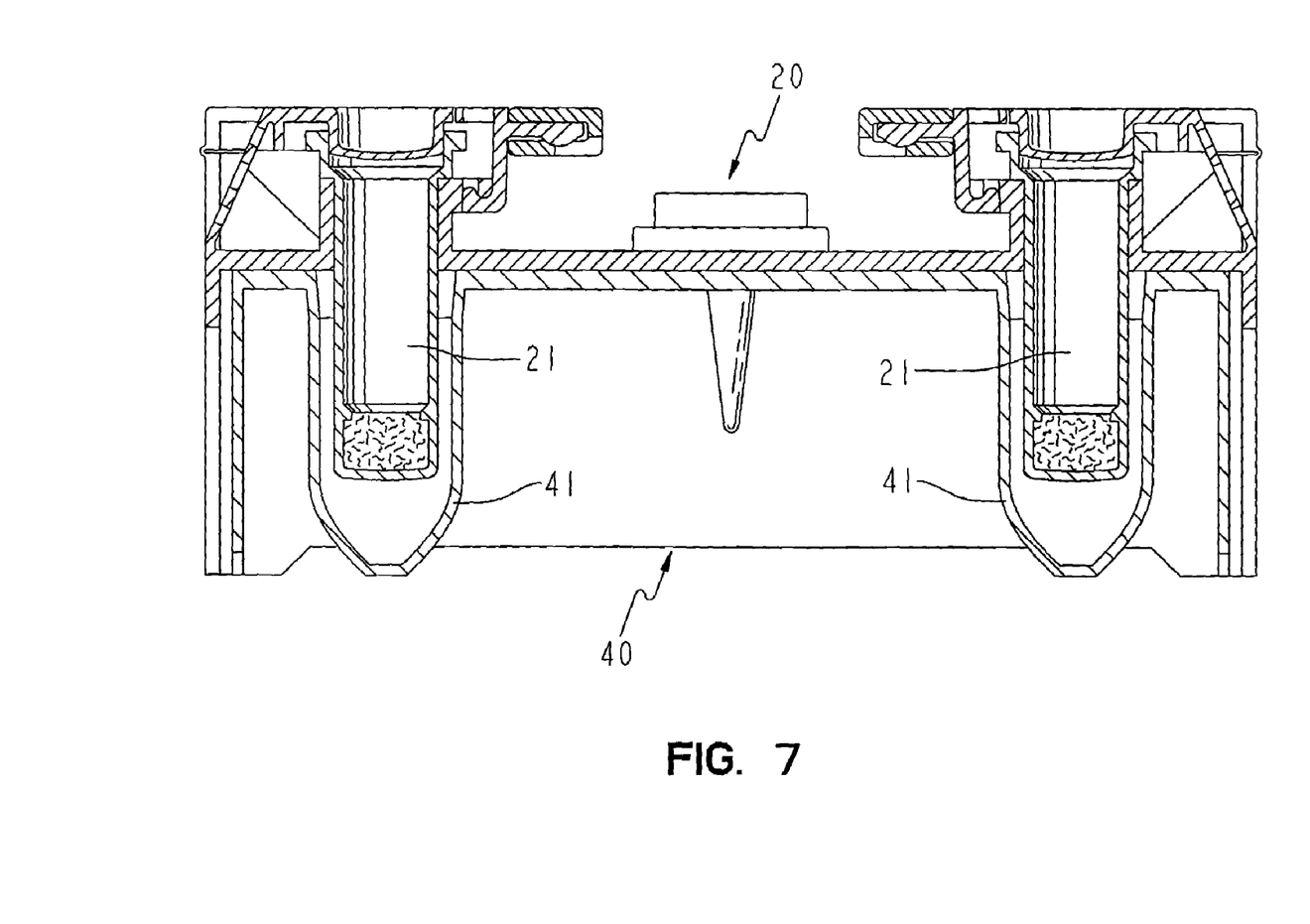
FIG. 7 shows a cross-section through an arrangement of matrix unit and collecting unit.

The interaction between the matrix unit and collecting unit is shown in greater detail in FIG. 7. FIG. 7 shows a cross-section through an arrangement of matrix unit and collecting unit. The matrix unit (20) with the matrix vessels (21) which hang in it is arranged on the collecting unit in such a way that the matrix vessels (21) extend into the collecting vessels (41). When biological materials are eluted from the matrices, the elution fluid thus passes directly into the collecting vessels (41).

Figure 8A:
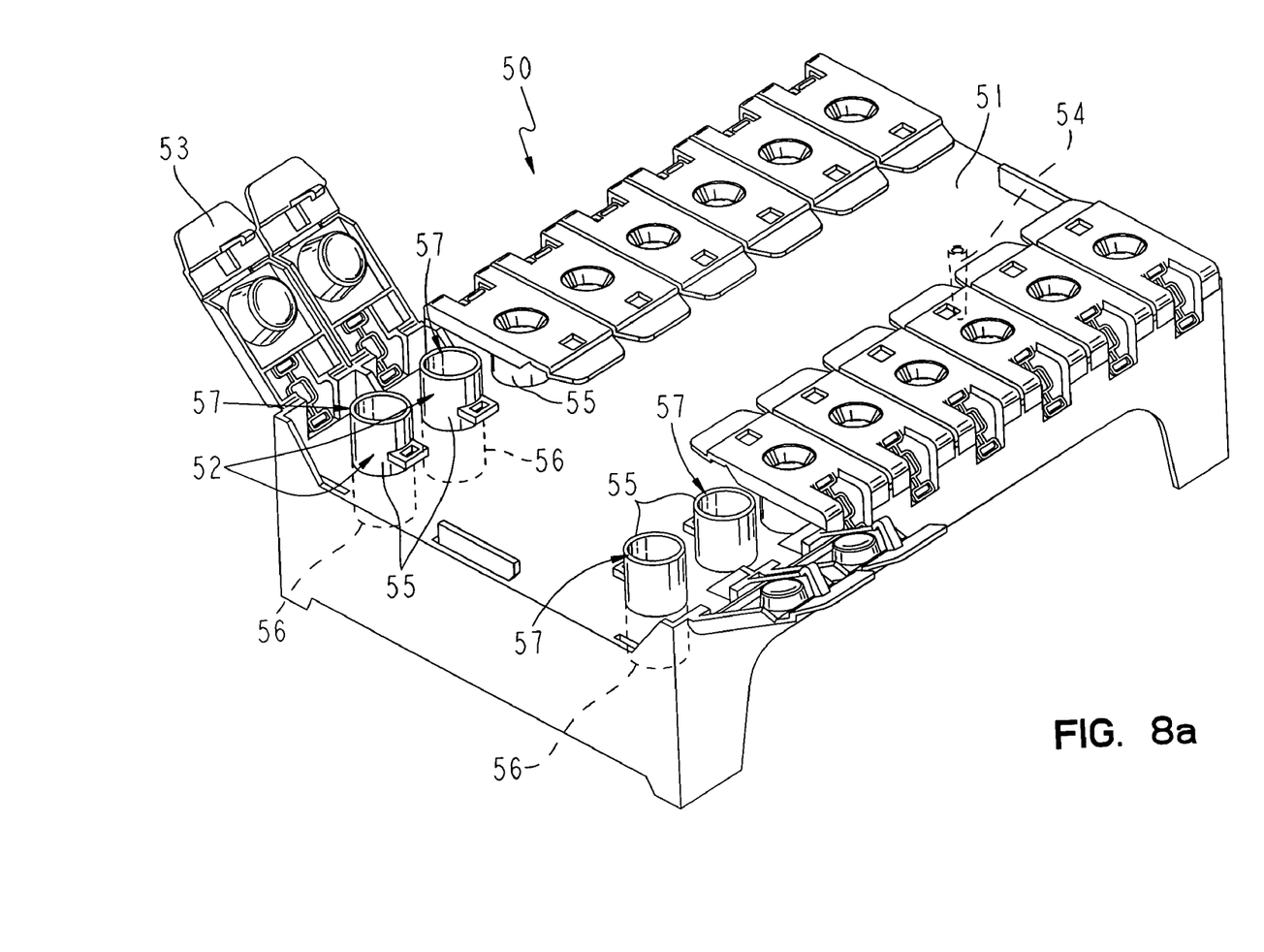
FIG. 8a shows in a perspective view that the collecting unit can be closed with the closure unit.

After the elution is completed, the matrix unit is removed from the collecting unit and the collecting unit can be closed with the closure unit shown in FIG. 8a. The closure unit (50) has a holder (51) in which two rows of eight tubes (52) are located. The tubes (52) have a part (55) which protrudes above the holder (51) and has a discharge opening (57) as well as a part (56) which extends below the holder (51) and has a connecting opening (59). The upper parts (55) of the tubes (52) and thus the discharge openings (57) are closed by caps (53). The closure unit (50) also has a tapered pin (54), which ensures an unequivocal orientation of the closure unit (50) relative to the collecting unit (40).

Figure 8B:
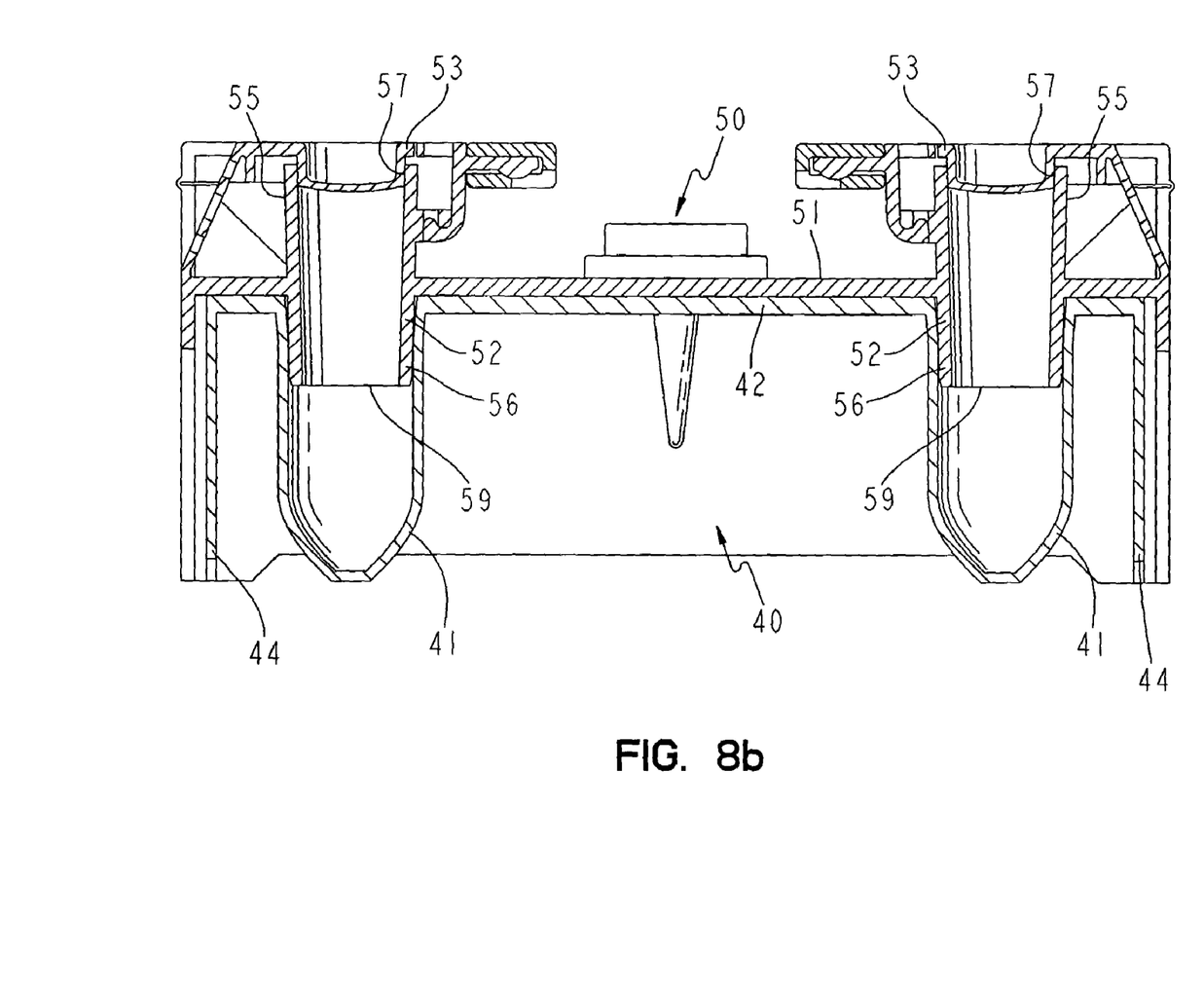
FIG. 8b shows an arrangement of the closure unit and the collecting unit.

An arrangement of closure unit (50) and collecting unit (40) is shown in FIG. 8b. This figure shows that the parts (56) of the connecting tubes (52), which extend downwards fit into the collecting vessels. For this purpose the lower ends of the connecting tubes (52) are preferably bevelled to facilitate the fitting in the openings of the collecting vessels. When the closure unit (50) is arranged on the collecting unit (40), the connecting tubes (52) make a liquid-tight fit in the collecting vessels. This can be achieved either by a shape fit or a press fit between the collecting vessel and connecting tube. In addition to the embodiment shown in FIG. 8 in which the connecting tube (52) engages in the collecting vessel, an embodiment is also possible in which the connecting tube embraces the outer contour of the collecting vessel.

FIG. 8 shows connecting tubes with a circular cross-section. However, other cross-sections, which differ from this such as ovals, rectangles and such like are also possible. However, the cross-section of the collecting vessels and connecting tubes are always matched to achieve a liquid-tight connection when the connecting unit is placed on the collecting unit.

Figure 9A:
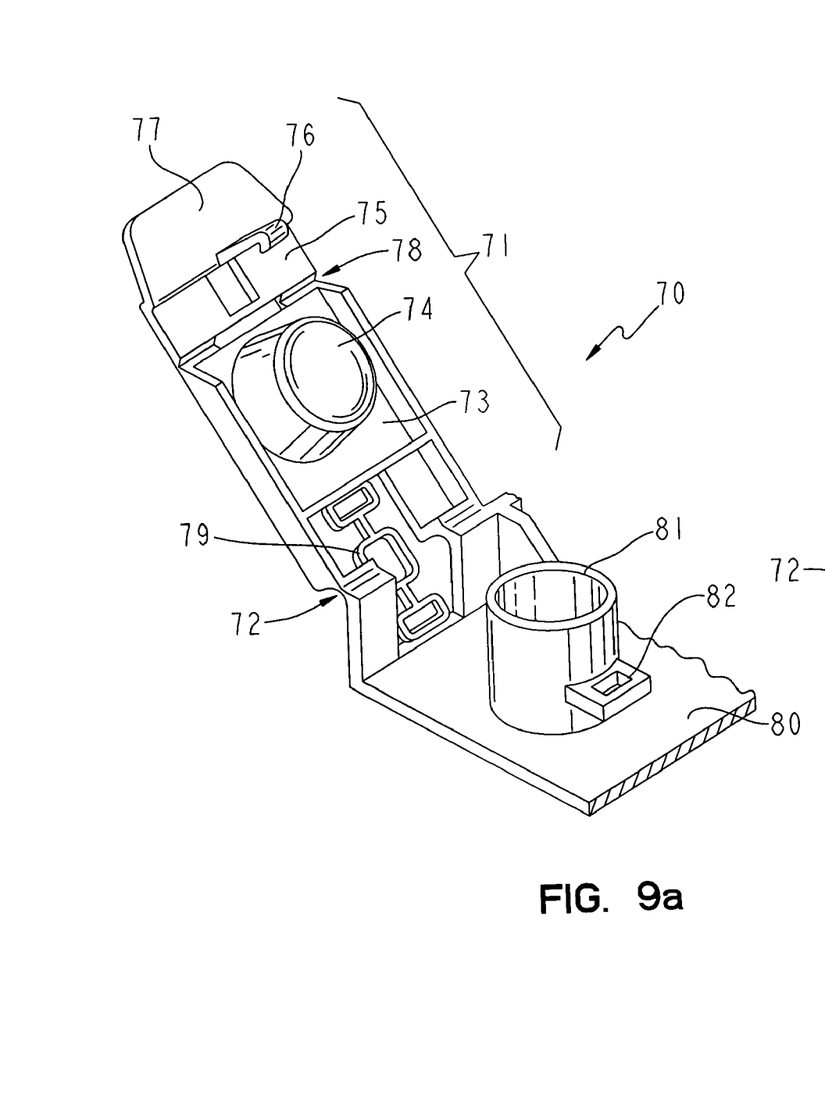
FIG. 9a shows the cap in the opened position.
Figure 9B:
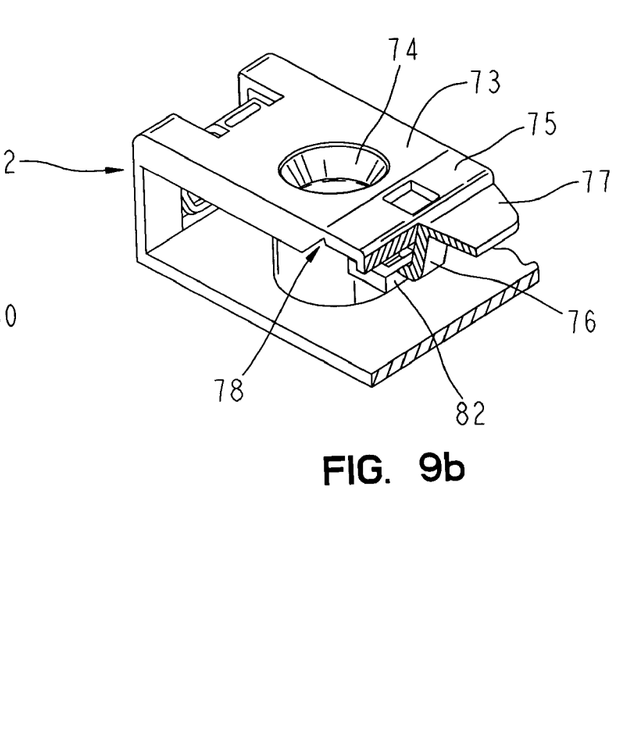
FIG. 9b shows the cap in the closed position.

A type of closure is shown in FIG. 9 that can be used advantageously for the lysis unit, matrix unit and closure unit. The cap shown is particularly suitable for the conditions that occur when providing biological materials. The closure arrangement has a cap (71), which is attached via a hinge (72) (preferably a film hinge) to a vessel or holder. There is a bulge (74) on the cap plate (73), which is used to close an opening. The bulge preferably has the shape of a truncated cone or spherical segment. A hook plate (75) is attached to the cap plate (73) via one or several hinges (78) (preferably film hinges). There is a hook (76) on this hook plate, which can be hooked in a ring. To improve the handling, the hook plate (75) has a handling tongue (77). As a result of the described hinges (72 and 78) the closure arrangement has two parts, which can be moved relative to a vessel or a holder. In addition the closure arrangement has a flexible part (79), which is attached to the cap plate (73) and a holder region (80). When the cap is swung from the opened position shown in FIG. 9a into a closed position, the cap passes a position in which the flexible part is stretched and at least partially relaxes again when it is swung further. The extension of the flexible part, which is at a maximum at a dead point causes the cap to either swing into an opened position or into a position in which its bulge (74) rests on the rim (81). In this position the opening is not yet closed liquid-tight, but the risk of contamination is greatly reduced. The cap can be opened again without a large exertion of force from the position in which the cap rests on the opening or the closure arrangement can be completely closed. In order to completely close the cap, the hook (76) can be hooked into a ring (82) by swinging the hook plate (75). Instead of the ring, the vessel can also have a lug under which the hook is hooked.

In the hooked position there is a pull on the cap plate (73) which presses the bulge (74) into the opening of the vessel and thus seals it gas and liquid-tight. If a liquid is heated in the vessel while the cap is clasped, the internal pressure in the vessel increases. However, the catch efficiently prevents the cap from springing open as a result of the interior pressure. This property of the described closure arrangement is particularly important for the lysis of sample liquids in which heating is carried out. In addition the closure arrangement can be used for vessels for thermocycling in which an elevated temperature is also used.

The volume of the cavities of the waste unit is preferably large enough that the washing liquids can be collected in addition to the lysis mixture without the liquid level touching the outlet opening of the matrix vessels.

If the bulge (74) has the shape of a truncated cone or of a spherical segment and the bulge is made of a flexible material, then an increase of the interior pressure of the vessel deforms the bulge such that the seal between the bulge and vessel rim is increased.

The hooked closure is opened by tilting the hook plate (75) against the cap plate (73). The design of the cap with two plates that can be swung in opposite directions provides a closure arrangement which can be closed and opened in a simple manner and with little effort and which ensures the sealing of a vessel even with an increased interior pressure.

LIST OF REFERENCE NUMERALS (1) sample
(2) pipette
(10) lysis unit
(11) lysis vessel
(12) cap of the lysis unit
(13) rail
(14) tapered pin
(15) plate
(20) matrix unit
(21) matrix vessel
(22) cap of the matrix unit
(23) tapered pin
(24) plate
(25, 25a) slot
(26) holder
(30) waste unit
(31) cavity
(32) partition
(33) tube
(34) tongue
(40) collecting unit
(41) collecting vessel
(42) holder
(43) hole
(44) standing element
(45) tongue
(50) closure unit
(51) holder
(52) connecting tube
(53) cap of the closure unit
(54) tapered pin
(60) coordination unit
(70) closure arrangement
(71) cap
(72) hinge
(73) cap plate
(74) bulge
(75) hook plate
(76) hook
(77) handling tongue
(78) hinge
(79) flexible part
(80) holding region
(81) rim
(82) ring

What is claimed is:

1. A process for isolating a purified biological material comprising:
   a) placing biological materials in separate lysis vessels of a lysis unit comprising two or several lysis vessels in a predetermined geometric arrangement,
   b) adding lysis liquids to the biological materials in the lysis vessels,
   c) transferring the liquids in the lysis vessels into a matrix unit containing matrix vessels with outlet openings whose number corresponds to the number of lysis vessels and a matrix is located in each of the matrix vessels to which the biological material to be purified binds,
   d) extracting by centrifugation the liquids in the matrix vessels through the outlet openings during which the liquids flow through the matrices,
   e) placing the matrix unit on a collecting unit with collecting vessels which are arranged such that at least the outlet openings of the matrix vessels extend into the collecting vessels,
   f) filling the matrix vessels with elution fluid,
   g) extracting the elution fluids from the matrix vessels through their outlet openings during which the elution fluids flow through the matrices and the elution fluids which are enriched with biological material are collected in the collecting vessels, and
   h) closing the collecting unit with a closure unit.

2. The process as claimed in claim 1, wherein biological materials are added to the lysis vessels by only opening the lysis vessel into which material is to be added and the caps of the other lysis vessels of the lysis unit are leaned to or closed.

3. The process as claimed in claim 1, wherein the caps of the matrix unit are in the leaned-to position before addition of the lysis liquids, a cap is opened for the addition and is brought into the closed position after the addition.

4. The process as claimed in claim 1 further comprising the steps:
  a) storing data which identify a biological sample,
  b) allocating the data relating to the biological sample to data which identify the lysis unit as well as the position of the lysis vessel within the lysis unit into which the sample is added,
  c) allocating data which identify the matrix unit into which the lysis liquids are added to data which identify the lysis unit,
  d) allocating data which either
     identify the collecting unit in which the elution liquid from the matrix unit is collected, or
     identify the closure unit used to close the collecting unit to the data for the matrix unit.

5. The process as claimed in claim 4, in which liquids are transferred from the lysis unit into the matrix unit by removing liquid from a lysis vessel and adding it to the matrix vessel of the matrix unit that is in a corresponding position.

* * * * *